United States Patent [19]

Manfredi et al.

[11] Patent Number: 4,980,164
[45] Date of Patent: Dec. 25, 1990

[54] STRAINS OF LACTOBACILLUS FOR ENHANCING FEED CONVERSION EFFICIENCY

[75] Inventors: Eugene T. Manfredi, Seattle; Robert E. Miller, Bellevue, both of Wash.

[73] Assignee: Bio Techniques Laboratories, Inc., Redmond, Wash.

[21] Appl. No.: 97,107

[22] Filed: Sep. 21, 1987

Related U.S. Application Data

[63] Continuation-in-part of Ser. No. 915,279, Oct. 2, 1986, Pat. No. 4,946,791.

[51] Int. Cl.$^5$ .................. A61K 35/74; C12N 1/20; A23K 1/00
[52] U.S. Cl. .................. 424/93; 435/252.9; 435/854; 426/2; 426/801
[58] Field of Search .................. 426/2, 801; 435/252.9, 435/854; 424/93

[56] References Cited

U.S. PATENT DOCUMENTS 3,343,962  9/1967  Peer .................. 426/41
4,689,226  8/1987  Nurmi et al. .................. 435/252.9
4,839,281  6/1989  Gorbach et al. .................. 435/34

FOREIGN PATENT DOCUMENTS 1134206  11/1968  United Kingdom .
1167196  10/1969  United Kingdom .................. 435/252.9

OTHER PUBLICATIONS

Mayra-Makinen et al, J. Appl. Bact., 55:241–245, 1983.
Mardh et al, Infect. Immun., Mar. 1976, pp. 661–666.
Sandine et al, J. Milk Food Technol., vol. 35 No. 12 (1972), 691–702.
Chan et al, Infect. Immun., Jan. 1985, pp. 84–89.
Jones, in Microbial Interactions (Receptors and Recognition: Series B, vol. 3), Reissig, J. L., ed. (1977), pp. 141–176.
Suegara et al, Infect. Immun., Jul. 1975, pp. 173–179.
Sherman et al, Appl. Environ. Micro., Aug. 1986, pp. 302–304.
Fuller et al, Am. J. Clin. Nutr., 27 (Nov. 1974), pp. 1305–1312.
Barrow et al., J. Appl. Micro. (1980), 48, 147–154.
Fuller, J. Appl. Bacteriol. (1978), 45, 389–395.

Primary Examiner—Jacqueline Stone
Attorney, Agent, or Firm—Christensen, O'Connor, Johnson & Kindness

[57] ABSTRACT

New strains of Lactobacillus capable of adhering to the gut epithelial cells of various species of animals and useful as dietary supplements.

3 Claims, No Drawings

STRAINS OF LACTOBACILLUS FOR ENHANCING FEED CONVERSION EFFICIENCY

FIELD OF THE INVENTION

This invention relates to novel microorganisms, particularly to strains of the bacteria *Lactobacillus acidophilus* (hereinafter "*L. acidophilus*") which are capable of interspecific attachment to epithelial cells of various animals, and to a process for providing a source of such microorganisms in an animal in the form of dietary supplements.

BACKGROUND OF THE INVENTION

Lactobacillus is a genus of bacteria in the family Lactobacteriacae, found in the intestinal tract of mammals, green plants, milk and fermenting foods. Lactic acid is produced by these bacteria via carbohydrate fermentation; thus, lactobacilli have been introduced into the manufacture of food products, such as yogurt and cheese, to enhance their quality and stability. In addition, lactobacilli form an important part of the internal microbial flora in humans and other animals. In humans, lactobacilli are present in the mouth, lower intestine and vagina.

Another type of bacteria, *Eschericia coli* (hereinafter, *E. coli*), is also present in animals and can cause serious intestinal problems such as diarrhea. The disease gastroenteritis is also caused by *E. coli* infection. A proper balance of the microbial populations in the intestinal tract of animals is believed to be important to provide resistance to such diseases. For a review, see W. E. Sandine et al., *J. Milk Food Technol.*, 35, p. 691–702 (1972), incorporated by reference herein. Stress conditions can alter the balance of microbes in the intestinal tracts of humans and other animals. The basis of diseases such as gastroenteritis is thought to be a microbial imbalance in the intestinal tract. This knowledge of the importance of maintaining internal populations of "helpful" bacteria such as lactobacilli to improve health has led to attempts to administer lactobacillus to treat humans and animals. *L. acidophilus* has shown some effectiveness in destroying *E. coli* in infants suffering from diarrhea. Such therapy has included the use of strains of *L. acidophilus* in dried form, administered orally, for promoting *L. acidophilus* colonization in human intestines.

*L. acidophilus* has also been used in animal feed in an attempt to restore and stabilize the internal microbial balance. In some cases, animals such as pigs were found to grow better and exhibited a decreased population of *E. coli* when administered lactobacilli. Two patents (U.S. Pat. No. 3,343,962 and British Patent No. 1,134,206) have been issued on methods of preparation of certain lactobacilli for use in animal feed supplements.

Unfortunately, in field studies outside of the laboratory, prior preparations using known strains of Lactobacillus have proven ineffective, in part because sufficiently high numbers of viable microorganisms are not present in the preparations and the organisms have not been able to successfully colonize the subject being treated. It is thought that adhesion is a primary event in colonization by bacteria of a particular habitat, such as the intestinal tract. Bacteria are known to adhere to various surfaces, including human and animal cells. G. W. Jones, "The Attachment of Bacteria to the Surfaces of Animal Cells," in *Microbial Interactions* (Russig Ed.), Chapman and Hall, London (1977), incorporated by reference herein. Colonization by bacteria also appears to be important for the establishment and maintenance of both normal and disease-associated bacterial flora in humans and other animals. For example, the ability of bacteria to attach to human mucosal epithelial cells, such as vaginal cells, has been studied for possible correlation with the subsequent colonization by pathogens and bacterial invasion of underlying tissues. R. A. Mardh and L. Westrom, *Infection and Immunity*, 13, p. 661–666 (1976); Chan et al., *Infection and Immunity*, 47, p. 84–89 (1985).

Distinct differences between strains of *Lactobacillus acidophilus* exist in their ability to survive, initiate and maintain a population within the intestine due, in part, to differences in the ability of the various strains to adhere to the epithelial cells of different species of animals. These differences may hamper the effectiveness of the administered bacteria. Prior known strains of lactobacilli demonstrate species specificity, such that one strain of *Lactobacillus acidophilus* from a chicken source will not adhere to epithelia of a different species, e.g., a rat, as shown by N. Suegara et al., *Infection and Immunity*, 12, p. 173–179 (1975); and R. Fuller, *J. Applied Bact.*, 45, p. 389–395 (1978). The stomach and intestinal tract also present physical challenges to the growth and survival of microorganisms, such as Lactobacillus, including the removal mechanism of the small intestine which washes out any organisms which cannot attach to the intestinal epithelial cells or multiply fast enough to avoid dilution.

It is believed that bacteria may attach to animal cells through a variety of mechanisms. In one system, cations may provide a bridge via ionic attraction between surfaces of the bacteria and epithelial cells. This system appears to be nonspecific and is calcium dependent. In another mechanism, the bacteria appear to attach by contacting receptor sites on the epithelial cells. This system is calcium independent and has been found to be species specific, suggesting that the ability to adhere (i.e., to recognize receptors) when mediated by this mechanism is under the genetic control of the species. At least one researcher has identified two subpopulations of human *Lactobacillus acidophilus* wherein one population requires calcium to adhere to human fetal epithelial cells. One of these strains is capable of interspecific attachment. Attachment of the other was found to be independent of calcium. This calcium independence has been found in only a few other human bacterial strains. E. G. Kleeman and T. R. Klaenhammer, *J. Diary Sci.*, 65, p. 2063–2069 (1982). Other mechanisms of attachment may be involved. Sherman et al., *Appl. Environ. Microbiol.*, 52, p. 302–304 (1986); Fuller et al., *Am. J. Clin. Nutr.*, 27, p. 1305–1312 (1974).

In addition to the difficulties of isolating a *Lactobacillus acidophilus* strain capable of adhering to the tissue of various species of animals, difficulties in culturing the strains exist.

SUMMARY OF THE INVENTION

Accordingly, the present invention provides new strains of Lactobacillus capable of adhering interspecifically to animal cells. Two strains, ATCC No. 53545 and No. 53673, also exhibit calcium-independent attachment; the attachment of these strains is enhanced, however, by the presence of calcium. The invention also describes a composition for use as a dietary supplement in animals containing the new strains of Lactobacillus in a suitable carrier such as a sugar carrier. The composition may be used to provide a source of the new strains of bacteria in an animal.

DETAILED DESCRIPTION OF THE INVENTION

The present invention describes biologically pure cultures of novel strains of *Lactobacillus acidophilus* and *helveticus* which are capable of attaching interspecifically to the tissue of animal species, including human, bovine, poultry and porcine tissue. In two strains, designated BT1386 and BT1870, attachment occurs independent of the presence of calcium, but may be enhanced by the addition of calcium. The novel strains of Lactobacillus may be used as a food additive, for example, as a supplement to commercial cattle feed, to provide a source of lactobacilli within the animal. The bacteria may benefit the animal host by improving the efficiency of conversion of food consumed by the animal.

Isolation

The novel strains of *Lactobacillus acidophilus*, —strains BT1386, BT1005, BT1507, BT1870, (*L. helveticus*), BT1808, and BT1806—were produced using selection and screening procedures, as described below, from bacteria isolated from cattle feces, human infant feces, pig feces, turkey intestine, chicken intestine, and pig intestine, respectively. For each animal, portions of feces, chyme or tissue were plated on MRS agar (Oxoid Ltd., Hants, England), and presumptive *L. acidophilus* colonies were identified by observing the morphology of the bacterial colonies and selecting flat, dry, white-appearing colonies.

Bacterial colonies, identified as described above, were subcultered three times as single colonies on MRS agar. *L. acidophilus* colonies were identified by observing carbohydrate utilization patterns using standard DMS Rapid CH (carbohydrate) Strips available from API Analytab Products, Plainview, NY. This procedure also results in segregation of different strains of *L. acidophilus*.

Selection

Single colonies of *L. acidophilus* obtained from subculture were screened by exposure to low pH and bile to select for populations able to survive within an animal's intestinal tract, and were then placed in contact with various animal species' tissues to isolate populations of *L. acidophilus* capable of attachment. The colonies were grown in MRS agar and exposed to a range of pH solutions (HCl, pH 2 and 7.2). Surviving colonies were then exposed to bovine bile solution (Difco Laboratories, Detroit, MI) to select for colonies tolerant to 3% bile.

Pure colonies of *L. acidophilus*, isolated as described above, were given a strain designation. Strains BT1386, isolated from bovine feces, BT1005, from human feces, and BT1507, from pig feces, exhibited the ability to survive exposure to low pH and bile, and to bind to tissues of different animal species, as described below in Example I. Strains BT1870, isolated from turkey intestine, BT1808, isolated from chicken intestine, and BT1806, isolated from pig intestine, are described below in Example IV.

Cultures of novel *L. acidophilus* strains BT1386, BT1005, BT1507, BT1870, BT1808, and BT1806 have been deposited with the American Type Culture Collection (ATCC), 12301 Parklawn Drive, Rockville, MD, and have received accession numbers ATCC No. 53545, No. 53544, No. 53546, No. 53673, No. 53672, and No. 53671, respectively.

The following Examples are presented to illustrate the advantages of the present invention and to assist one of ordinary skill in making and using the same. The Examples are not intended in any way to otherwise limit the scope of the disclosure or the protection granted by Letters Patent hereon.

EXAMPLE I

In vitro attachment of *Lactobacillus acidophilus* strains BT1386, BT1005 and BT1507

Bacterial Culture

A substantially pure culture of *L. acidophilus* strain (BT1386) was inoculated as a 5% inoculum and incubated at 37° C. in 5% $CO_2$ for 24 hrs in MRS broth (Oxoid, Ltd.). 24 hour-old cultures were tested for adherence. Bacterial cultures were refrigerated or frozen when not in use.

Two other novel strains of *L. acidophilus* described herein, BT1005 and BT1507, were similarly cultured and stored. Other strains of *L. acidophilus* were used for comparison purposes; strain C7 was obtained from Dr. Klaenhammer, North Carolina State University, Raleigh, NC; strain 1336 was obtained from University Micro Reference Labs, Inc., Ann Arbor, MI. Both strains were cultured and stored as described above for BT1386.

Tissue Culture (a) Cell Lines

Epithelial cells (HFI) from human embryonic intestine, ATCC No. CCL6, Intestine No. 407, were obtained from the ATCC. Primary cell line from whole fetal bovine intestine (BFI) was obtained from Flow Laboratories, Inc., McLean, Va. Primary cell line from chick embryo intestine (CEI), and primary cell line from whole fetal porcine intestine (PFI), were prepared at Bio Techniques Laboratories, Inc., Redmond, WA. HFI cells were used from the 277th to the 298th passage; BFI cells were used from the third to the tenth passage; CEI cells were used from the third to the fourth passage; and, PFI cells were used from the third to the twentieth passage.

(b) Methods for Culture

The cells obtained as above were cultured in a monolayer with a growth medium of Eagle's minimal essential medium (MEM) supplemented with Earle's Salts (L-Glutamine, Non-essential Amino Acids with 15% fetal calf serum) (GIBCO Laboratories, Grand Island, NY). The pH of the medium was adjusted to approximately 7.2 and buffered with 5% $CO_2$ at the time of feeding or transfer. For adherence studies, the tissue cells were cultured in screw cap test tubes (16×100 mm) containing a glass cover slip (9×22 mm) for tissue cell attachment.

Preparation of Bacterial Cells for Adherence Tests

Twenty-four hour bacterial cultures in MRS broth were harvested by centrifuging for 5 minutes at ambient room temperature, washed three times in phosphate buffered saline, pH 7.2 (PBS: NaCl 8 g, $KH_2PO_4$ 0.2 g, $Na_2HPO_4$ 1.145 g, KCl 0.2 g/liter), and resuspended in 2 to 3 ml of Earle's Balanced Salt Solution (EBSS: KCl 0.4 g, NaCl 6.8 g, $NaHCO_3$ 2.2 g, $NaH_2PO_4$ 0.14 g, D-Glucose 1.0 g, Phenol Red 0.01 g/liter) with or without 3.4mM CaCl. This suspension was used to adjust additional EBSS, with or without 3.4mM CaCl, to an optical density (O.D.) of 0.60 to 600 nm using a Bausch and Lomb Spectronic 20 spectrophotometer (Rochester, N.Y.). The growth media was pipetted from the culture tubes containing cells attached to cover slips. EBSS heated to 37° C. was pipetted in, and drained out twice, to remove any free-floating cells.

Adherence of Bacteria to Tissue Cells

The method for testing bacterial attachment to tissue cells was the same for all strains of bacteria and all tissue cells lines. 3 mls of the 0.60 O.D. bacterial suspension was pipetted into the tube over the cover slip containing the monolayer, and the tube was incubated for 30 minutes at 37° C. After incubation, the bacterial suspension was removed, and the monolayer with attached cells was rinsed three times with EBSS to remove any nonattached bacteria, following the procedures described by Kleenman et al., supra, for sequential removal of bacteria attached to tissue cell monolayers. The cover slips were then fixed with acetone for 10 seconds and air dried. The cover slips where gram stained and viewed at 1000×magnification under oil immersion. Bacteria and tissue cells in 10 randomly selected fields were counted, and the bacteria-to-tissue cell ratio was calculated and designated the attachment frequency. The average attachment frequencies for human, bovine, poultry and porcine tissue cells for the novel strains of L. acidophilus and for selected known L. acidophilus strains are presented in Tables 1 through 4.

TABLE 1

ATTACHMENT OF LACTOBACILLUS ACIDOPHILUS STRAINS TO HUMAN FETAL INTESTINAL CELLS (HFI)

| Strain | BT1386 | | C-7 | | 1336 | | BT1005 | |
|---|---|---|---|---|---|---|---|---|
| 3.4 mM $CaCl_2$ present (+)/absent (−) | + | − | + | − | + | − | + | − |
| Attachment Frequency[1] (bacterial cells per tissue cell) | 19 | 3.6 | 3.68 | 0 | 0 | 0 | 7.4 | 4.9 |

[1]Represents an average value for up to 4 test runs.

TABLE 2

ATTACHMENT OF LACTOBACILLUS ACIDOPHILUS STRAINS TO BOVINE FETAL INTESTINAL CELLS (BFI)

| Strain | BT1386 | | C-7 | | 1336 | | BT1005 | |
|---|---|---|---|---|---|---|---|---|
| 3.4 mM $CaCl_2$ present (+)/ absent (−) | + | − | + | − | + | − | + | − |
| Attachment Frequency[1] (bacterial cells per tissue cell) | 6.67 | 4.28 | 0 | ND | 0 | ND | 0.5 | ND |

ND = Test Not Done
[1]Represents an average value for up to 4 test runs.

TABLE 3

ATTACHMENT OF LACTOBACILLUS ACIDOPHILUS STRAINS TO PORCINE FETAL INTESTINAL (PFI) CELLS

| Strain | BT1386 | | C-7 | | 1336 | | BT1005 | | BT1057 | |
|---|---|---|---|---|---|---|---|---|---|---|
| 3.4 mM $CaCl_2$ present (+)/ absent (−) | + | − | + | − | + | − | + | − | + | − |
| Attachment Frequency (bacterial cells per tissue cell) | 10 | 5.6 | 0 | 0 | 0 | 0 | 0 | 0 | 4.54 | 2.9 |

TABLE 4

ATTACHMENT OF LACTOBACILLUS ACIDOPHILUS STRAINS TO CHICK EMBRYO INTESTINE (CEI) CELLS

| Strain | BT1386 | | C-7 | | BT1005 | | BT1057 | |
|---|---|---|---|---|---|---|---|---|
| 3.4 mM $CaCl_2$ present (+)/ absent (−) | + | − | + | − | + | − | + | − |
| Attachment Frequency (bacterial cells per tissue cell) | 0.6 | ND | 0 | ND | 0.6 | ND | 5.3 | ND |

Tables 1–4 show that strain BT1386, a homofermentive gram positive rod isolated from cattle, attaches to human, bovine, poultry and porcine intestinal cells and that this attachment is independent of the presence of calcium. These results also demonstrate that, while this strain does not require calcium to attach to epithelial cells, the presence of additional calcium enhances the attachment of the bacteria to human, bovine and porcine cells.

Strain BT1005, a homofermentive gram positive rod isolated from a human, also shows attachment to human cells independent of the presence of calcium, and improved attachment in the presence of calcium. BT1005 also attaches to bovine and poultry cells in the presence of calcium.

Strain BT1057, a homofermentive gram positive rod obtained from pig feces, demonstrates calcium independent attachment and enhancement on porcine cells and attachment to poultry cells. Other L. acidophilus strains, C7 and 1336, do not show calcium independent attachment and fail to attach to the various tissue cells, except that C7 attaches to human intestine cells in the presence of calcium.

The novel strains of the present invention may be used as dietary supplements for animals (including humans) to provide an internal source of L. acidophilus. The bacteria may be administered along or in a carrier, or with other components, including vitamins, minerals, medications and other additives. For use as dietary supplements, the strains may be administered orally in a suitable, palatable carrier, for example, in a sugar carrier of D-glucose or dextrose, or using inert materials such as diatomaceous earth, starch and cellulose. The lactobacilli will typically be lyophilized, and should be protected from light, water and oxygen prior to hydration for use as a feed supplement. Dosage of the bacteria will vary according to the strain used and the animal subject. It was unexpectedly found, however, that there may be a maximum dosage of bacteria above which performance as a supplement is impaired, and such a dosage may even cause a reduction in the efficiency of feed conversion. Example II shows the effects of administering strain BT1386 to cattle as a feed supplement.

EXAMPLE II

The effect of oral administration and continuous feeding of *Lactobacillus acidophilus* strain BT1386 in a bovine model A field study was conducted on feedlot cattle (steers) in Amarillo, Texas during August 1985 to November 1985. Three different formulations of preparations containing lyophilized (freeze-dried) *L. acidophilus* strain BT1386 in a sugar carrier, and a fourth formulation consisting of a simple sugar carrier without the BT1386, as a control, were administered orally using a drenching gun to individual newly arrived cattle, followed by continuous feeding of solid feed with and without *L. acidophilus* for 84 days.

Test Animals

Forty-eight newly arrived feeder cattle (steers), of various sizes and weights (approximately 405 lbs each), were obtained by Dr. D. Hutchinson at Texas A & M University, Agricultural Experiment Station in Amarillo, Tex., from Tennessee, and were divided into four groups. Sixteen animals were assigned to each group, using a randomized complete block program for assignment. The four groups consisted of animals given a low, medium or high dose of *L. acidophilus* strain BT1386, as described below, and a control group to which no bacteria were administered.

Administration of Additive

Vials containing various formations of freeze-dried *Lactobacillus acidophilus* strain BT1386 for either liquid oral doses or solid feed additive oral doses were appropriately designated for each group. Doses consisted of high ($2 \times 10^{10}$ colony forming units (CFU) of strain BT1386 per animal per day), medium ($2 \times 10^8$ CFU), and low ($2 \times 10^6$ CFU), or controls containing the sugar carrier and no bacteria. A single liquid oral dose ("drench"), of approximately 10 ml of *L. acidophilus* in water, was administered to each animal on the first day of the test. Each animal received the same volume of the liquid by mouth, using a drench gun. During the solid feeding phase, treated feed was prepared on a daily basis by suspending the contents of one vial in one liter of clean water in a clean container and evenly distributing the material over the feed and mixing. The feed was then emptied into a labeled hopper.

To ensure that the cattle took in the full dose of bacteria, the average minimum amount of intake of feed per day, per animal, was predetermined, and the full dose incorporated into that amount of feed. Treated feed left over from the previous day was discarded.

Measurements

Measurements were taken of the initial weight of each individual animal, in pounds, on arrival at the feed lot. Daily feed intake was measured to determine total feed intake per animal, per day, and this data was recorded by an on line computer for constant processing. Each animal was weighed at 28-day intervals after the initial weighing, and a final weight taken after 84 days at the end of the study. Observations on general health of the animals were made at the start, at weekly, and at the conclusion of the study.

Data Analysis

The one-way statistical analysis of variance technique was used to analyze weight gains, feed intakes, and feed conversion data. Feed conversion is a measure of the amount of feed required for the animal to gain one pound of weight, and may be calculated by dividing intake by weight gain for a given time period. Table 5 shows the mean feed conversion for the four test groups after 84 days. Statistical significance of the results is indicated by comparing calculated Least Significant Differences (LSD) with the predicted LSC values obtained from the analysis of variance. Feed conversion values which result in a calculated LSD which exceeds the predicted LSD are considered significant.

TABLE 5

FIELD TEST OF BT1386 IN FEEDLOT CATTLE (84 DAY DATA)

| Group | Mean Feed Conversion | Calculated LSD[1] |
|---|---|---|
| Control | 6.012 | |
| High | 6.355 | NS[2] |
| Medium | 5.472 | 0.883 |
| Low | 5.536 | 0.819 |
| Predicted LSD[3] | 0.550 | |

[1]LSD = Least Significant Difference
[2]NS = Not Significant
[3] = Significant at Alpha = 0.05

As can be seen from Table 5, feed conversions for animals receiving medium and low doses of strain BT1368 were significant. Animals receiving a medium dose of *L. acidophilus* BT1368 consumed the most food and gained the most weight, and were the most efficient in converting feed into weight gain, as compared to animals receiving the other doses or the control.

These results indicate that the response in the animals to *L. acidophilus* BT1386 is dose dependent, with medium doses demonstrating the best feed conversion. Surprisingly, these results also show that high doses of bacteria lead to reduced feed conversion, as compared to animals in the control group, suggesting that there is a strain-specific maximum dose above which performance of the bacteria is impaired and the efficiency of feed conversion is reduced.

EXAMPLE III

The effect of administration of *Lactobacillus acidophilus* strain BT1386 in poultry Tests were also run in a 49-day study at Bio Techniques Laboratories, Inc. (Redmond, WA), using BT1386 as a feed supplement for Cornish Cross poultry. Poultry fed water containing strain VT1386 also demonstrated superior feed conversion over controls (lacking bacteria) with poultry fed high doses ($1 \times 10^9$ CFU/bird day) exhibiting better feed conversion than those fed low doses ($1 \times 10^8$ CFU/bird day). This dose response may be due, in part, to the fact that antibiotic, which may depress the effective number of introduced bacteria, was present in poultry feed to mimic industry feeding conditions.

EXAMPLE IV

Strains BT1870, BT1808, and BT1806 were isolated using the selection and screening procedures described above.

BT1870 is a homofermentive gram-positive-rod strain of *Lactobacillus helveticus*, isolated from turkey intestine, that attaches to human fetal intestine as well as to turkey crop and cecal cells. The attachment of BT1870 is calcium independent, but is enhanced by $Ca^{++}$.

*L. acidophilus* strains BT1808 and BT1806 were isolated from chicken and pig intestines, respectively, and exhibit calcium-dependent attachment to gut epithelial cells.

While the present invention has been described in conjunction with preferred embodiments, one of ordinary skill, after reading the foregoing specification, will be able to effect various changes, substitutions of equivalents and alterations to the compositions and methods set forth herein. It is therefore intended that the protection granted by Letters Patent hereon be limited only by the appended claims and equivalents thereof.

The embodiments of the invention in which an exclusive property or privilege is claimed are defined as follows:

1. A composition for use as a dietary supplement to increase feed conversion efficiency in an animal, comprising *Lactobacillus acidophilus* strain ATCC No. 53545, in a carrier suitable for administration to an animal.

2. A process for providing a source of Lactobacillus to increase feed conversion efficiency in animals, comprising administering *Lactobacillus acidophilus* strain ATCC No. 53545 to an animal.

3. A process for providing a dietary source of Lactobacillus to increase feed conversion efficiency in animals, comprising dispensing and delivering a dietary supplement comprising *Lactobacillus acidophilus* strain ATCC No. 53545 into livestock feed.

* * * * *